United States Patent [19]
Goda et al.

[11] Patent Number: 5,756,806
[45] Date of Patent: May 26, 1998

[54] CYANOBENZENESULFENYL HALIDE AND PROCESS FOR PREPARATION OF 3-SUBSTITUTED BENZISOTHIAZOLE USING THE SAME

[75] Inventors: Hiroshi Goda; Junichi Sakamoto; Shigeki Sakaue; Sakae Kajihara; Miki Todo, all of Hyogo-ken, Japan

[73] Assignee: Sumitomo Seika Chemicals Co., Ltd., Hyogo, Japan

[21] Appl. No.: 861,426

[22] Filed: May 21, 1997

Related U.S. Application Data

[62] Division of Ser. No. 630,730, Apr. 10, 1996, Pat. No. 5,679,827.

[30] Foreign Application Priority Data

Apr. 24, 1995 [JP] Japan ................................ 7-098387

[51] Int. Cl.⁶ .......................................... C07C 255/49
[52] U.S. Cl. .................................................. 558/425
[58] Field of Search ..................................... 558/425

[56] References Cited

U.S. PATENT DOCUMENTS

| 4,140,692 | 2/1979 | Fleig et al. | 548/212 |
| 4,590,196 | 5/1986 | Smith et al. | 514/253 |
| 4,745,117 | 5/1988 | Ishizumi et al. | 514/254 |
| 5,359,068 | 10/1994 | Urban | 544/368 |

FOREIGN PATENT DOCUMENTS

| 536512 | 4/1993 | European Pat. Off. |
| 2343734 | 10/1977 | France |
| 63-083067 | 5/1988 | Japan |
| 63-083085 | 7/1988 | Japan |
| 2163432 | 2/1986 | United Kingdom |

OTHER PUBLICATIONS

Beck, J. R., et al., J. Org. Chem., 43, No. 8, 1604–1606 (1978).
Bryce, M. R., et al., J. Chem. Soc., Perkin Trans. I(8), 2141–2144 (1988).
Yevich, J. P., et al., J. Med. Chem., 29(3), 359–369 (1986).

Primary Examiner—Johann Richter
Assistant Examiner—Ebenezer Sackey

[57] ABSTRACT

The present invention provides a compound represented by the general formula (I):

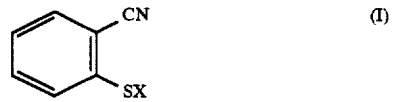

wherein X represents Cl or Br, a process for preparation of the same and a process for preparation of 3-substituted benzisothiazole by reaction of the compound (I) with a piperazine compound.

4 Claims, No Drawings

CYANOBENZENESULFENYL HALIDE AND PROCESS FOR PREPARATION OF 3-SUBSTITUTED BENZISOTHIAZOLE USING THE SAME

This is a divisional of application Ser. No. 08/630,730 filed on 10 Apr. 1996 now Pat. No. 5,679,827.

FIELD OF THE INVENTION

The present invention relates to novel 2-cyanobenzenesulfenyl halide and a process for preparation of the same, as well as a novel process for preparation of 3-substituted benzisothiazole using the same compound. 2-Cyanobenzenesulfenyl halide is a novel compound which has not been previously known, and is a useful compound, in particular, as an intermediate upon preparation of a 3-substituted benzisothiazole derivative important as an intermediate for preparation of pharmaceuticals.

BACKGROUND OF THE INVENTION

Hitherto, as a process for preparation of 3-substituted benzisothiazole derivatives, there have been known a number of processes by reacting 3-halo-1,2-benzisothiazole with a piperazine compound according to the following Reaction Scheme:

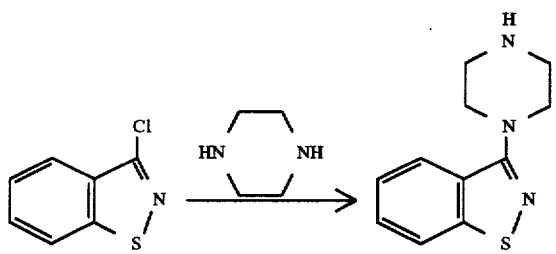

See JP-A 63-83067; JP-A 63-83085; EP-A 196096; J. Chem. Soc., Perkin. Trans., 1(8), 2141, 1988; Ger. Offen., 3530089; J. Med. Chem., 29(3), 359, 1986; J. Org. Chem., 43(8), 1604, 1978.

OBJECTS OF THE INVENTION

However, 3-halo-1,2-benzisothiazole used in the above known processes as a raw material is not easily available. A method for chlorinating 1,2-benzisothiazol-3-one and a method using thiosalicylic acid as a starting material are described in the above references. However, these methods use an expensive raw material, have the lower yield and, therefore, they are not said to be industrially advantageous.

As described above, it was difficult to advantageously prepare 3-substituted benzisothiazole derivatives on the industrial scale.

Accordingly, one object of the present invention is to provide an industrially advantageous process for preparation of 3-substituted benzisothiazole derivatives.

Another object of the present invention is to provide a useful intermediate which can be used upon preparation of a 3-substituted benzisothiazole derivative.

Still another object of the present invention is to provide a process for preparation of the above intermediate.

Theses objects as well as other objects and advantages of the present invention will become apparent to those skilled in the art from the following description.

SUMMARY OF THE INVENTION

In view of the above circumstances, the present inventors studied hard in order to provide an industrially advantageous process which can prepare a 3-substituted benzisothiazole derivative easily and economically without the use of expensive raw materials. As the result, we found that 2-cyanobenzenesulfenyl halide represented by the formula (I) below can be an important intermediate for preparation of a 3-substituted benzisothiazole derivative, investigated the physical properties of the halide and studied hard to provide an industrially advantageous and easy process for preparation of the halide and the 3-substituted benzisothiazole derivative.

2-Cyanobenzenesulfenyl halide is a novel compound which has never been described in the literature and the physical properties thereof and a process for preparation of the same are not known.

That is, the present inventors found that the present novel 2-cyanobenzenesulfenyl halide can be easily obtained by halogenating a 2-cyanophenylthio derivative represented by the general formula (II) below, and a 3-substituted benzisothiazole derivative can be easily obtained by reacting the 2-cyanobenzenesulfenyl halide with a piperazine compound.

Further, the present inventors found that 3-substituted benzisothiazole derivative can be effectively obtained by a process by successively performing the above two reactions, that is, by halogenating a 2-cyanophenylthio derivative to obtain 2-cyanobenzenesulfenyl halide which is subsequently reacted with a piperazine compound.

The present invention was completed by our such the findings and it provides:

(1) 2-cyanobenzenesulfenyl halide represented by the general formula (I):

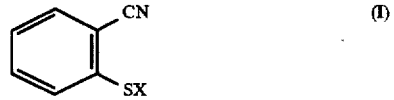

wherein X represents Cl or Br, (2) a process for preparation of 2-cyanobenzenesulfenyl halide represented by the general formula (I) which comprises halogenating a 2-cyanophenylthio derivative represented by the general formula (II):

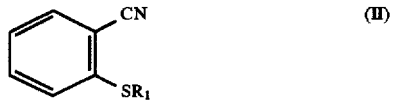

wherein $R_1$ represents H, alkaline metal, 2-cyanophenylthio group or straight or branched alkyl group having 1 to 4 carbon atoms, (3) a process for preparation of 3-substituted benzisothiazole represented by the general formula (IV):

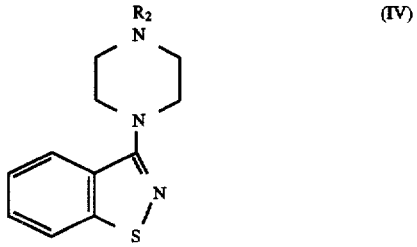

wherein $R_2$ represents H, alkyl group having 1 to 6 carbon atoms or substituted alkylene group having 1 to 6 carbon atoms, which comprises reacting 2-cyanobenzenesulfenyl halide represented by the general formula (I) with a piperazine compound represented by the general formula (III):

wherein $R_2$ is as defined in the general formula IV, and (4) a process for preparation of 3-substituted benzisothiazole represented by the general formula (IV) which comprises halogenating a 2-cyanophenylthio derivative represented by the general formula (II) to obtain 2-cyanobenzenesulfenyl halide represented by the general formula (I), then reacting the halide represented by the general formula (I) with a piperazine compound represented by the general formula (III).

DETAILED DESCRIPTION OF THE INVENTION

The present invention is explained in detail below.

In a novel compound, 2-cyanobenzenesulfenyl halide represented by the general formula (I), a group represented by X is Cl or Br. That is, the compound represented by the general formula (I) is 2-cyanobenzenesulfenyl chloride or 2-cyanobenzenesulfenyl bromide.

The compound represented by the general formula (I) can be prepared by halogenating a 2-cyanophenylthio derivative represented by the general formula (II).

Group $R_1$ in the compound represented by the general formula (II) is H, alkaline metal such as sodium, potassium and the like, 2-cyanophenylthio group, straight or branched alkyl group having 1 to 4 carbon atoms such as methyl, ethyl, n-propyl, isopropyl, n-butyl, t-butyl and the like. The particular compounds represented by the general formula (II) are 2-cyanobenzenethiol, 2,2'-dicyanodiphenyl disulfide, 2-cyanophenyl methyl sulfide, 2-cyanophenyl ethyl sulfide, 2-cyanophenyl n-propyl sulfide, 2-cyanophenyl isopropyl sulfide, 2-cyanophenyl n-butyl sulfide, 2-cyanophenyl t-butyl sulfide and the like.

For halogenating the compound represented by the general formula (II), chlorine, sulfuryl chloride, bromine, sulfuryl bromide, and a mixture thereof can be used as a halogenating agent. Among them, chlorine and bromine are preferable. An amount of a halogenating agent to be used varies depending upon a kind of the compound represented by the general formula (II) and is usually in a range of 0.5 to 7-fold in mole terms relative to the compound represented by the general formula (II).

A reaction temperature for halogenation varies depending upon a kind of the compound represented by the general formula (II) and is usually in a range of about $-10°$ C. to about 160° C., preferably about $-5°$ C. to about 130° C. When a reaction temperature is too low, the reaction rate becomes slow. On the other hand, when a reaction temperature is too high, side reactions occur, which leads to the decreased yield.

The halogenating reaction can be carried out without any solvent or in a solvent. Examples of the solvent are, not limited to, hydrocarbon such as hexane, cyclohexane, heptane and the like, halogenated hydrocarbon such as dichloroethane, dichloromethane, chloroform and the like, aromatic hydrocarbon such as benzene, toluene, xylene, chlorobenzene, dichlorobenzene, trichlorobenzene and the like, polar solvent such as N,N-dimethylformamide, dimethyl sulfoxide and the like. When a solvent is used, an amount of the solvent to be used is usually, not limited to, 0.1 to 10-fold in weight terms relative to the compound represented by the general formula (II).

2-Cyanobenzenesulfenyl halide, thus obtained, represented by the general formula (I) can be isolated by the conventional method such as distillation, crystallization or the like.

2-Cyanobenzenesulfenyl halide, thus obtained, represented by the general formula (I) can be reacted with a piperazine compound represented by the general formula (III) to obtain 3-substituted benzisothiazole represented by the general formula (IV).

Examples of the piperazine compound are piperazine, 1-alkyl-piperazine such as 1-methyl-piperazine, 1-ethyl-piperazine, 1-n-butyl-piperazine and the like, and 1-substituted alkylene-piperazine such as 1-imidobutylene-piperazine, 1-amidobutylene-piperazine, 1-((5-indole)ethylene)-piperazine and the like.

An amount of the piperazine compound to be used is usually in a range of 1 to 10-fold, preferably 3 to 6-fold in mole terms relative to 2-cyanobenzenesulfenyl halide represented by the general formula (I).

A reaction temperature is usually in a range of about 80° C. to about 150° C., preferably about 100° C. to about 130° C. When a reaction temperature is too low, the reaction rate becomes slow. On the other hand, when a reaction temperature is too high, side reactions occur, which leads to the decreased yield.

A solvent is not necessarily required and a reaction is preferably carried out without a solvent. Alternatively, the reaction may be carried out in a solvent. Examples of the solvent are hydrocarbon such as cyclohexane, heptane and the like, aromatic hydrocarbon such as benzene, toluene, xylene, chlorobenzene, dichlorobenzene, trichlorobenzene and the like, and polar solvent such as N,N-dimethylformamide, dimethyl sulfoxide and the like. When a solvent is used, an amount of the solvent to be used is usually, not to limited to, in a range of 0.1 to 10-fold in weight terms relative to the compound represented by the general formula (I).

3-Substituted benzisothiazole, thus obtained, represented by the general formula (IV) can be isolated from a reaction mixture and purified by the conventional method such as crystallization or the like.

Examples of the particular 3-substituted benzoisothiazole are 3-(1-piperazinyl)-1,2-benzisothiazole, 3-(4-ethyl-1-piperazinyl)-1,2-benzisothiazole, 3-(4-n-butyl-1-piperazinyl)-1,2-benzisothiazole, 3-(4-cyclohexyl-1-piperazinyl)-1,2-benzisothiazole and the like. These compounds can be isolated as a mineral acid salt such as hydrochloride, sulfate or the like under acidic conditions in the presence of hydrochloric acid, sulfuric acid or the like.

3-Substituted benzisothiazole represented by the general formula (IV) can also be prepared by a process where the above two reactions are successively carried out in series, that is, by halogenating 2-cyanophenylthio halide represented by the general formula (II) to obtain 2-cyanobenzenesulfenyl halide represented by the general formula (I) which is subsequently reacted with a piperazine compound represented by the general formula (III).

An halogenating reaction and a reaction with the piperazine compound in this process can be carried out as described for each reaction.

A compound represented by the general formula (II) used as a raw material for preparation of a compound represented by the general formula (I) can be easily obtained according to a present inventor's process described in Japanese patent application No. 6-289763. That is, 2-cyanochlorobenzene is converted into 2-cyanophenyl methyl sulfide with a sodium salt of methylmercaptane, then the methyl group thereof is halogenated and hydrolyzed to obtain 2-cyanobenzenethiol, which is further treated with an alkali to obtain an alkaline metal salt thereof, which is oxidized to obtain 2,2'-dicyanodiphenyl disulfide.

The following Examples illustrate the present invention in detail but are not to be construed to limit the scope thereof.

EXAMPLE 1

67.5 g (0.500 mol) of 2-cyanobenzenethiol and 150 g of chlorobenzene were placed in a 300 ml four-neck flask equipped with a stirrer, a thermometer, a chlorine blowing inlet and a condenser and 39 g (0.55 mol) of chlorine was blown therein at about 80° C. over 2 hours while stirring. The solvent was distilled, followed by evaporation under reduced pressure to obtain 81.7 g of white crystals, which were identified to be 2-cyanobenzenesulfenyl chloride from the following data. The yield starting from 2-cyanobenzenethiol was 96.4%.

Physical properties
2-Cyanobenzenesulfenyl chloride
Appearances: white crystals
Melting point: 38.5°–39.0° C.
NMR: δ (ppm) 7.37–8.09 (m)
IR: (KBr, cm$^{-1}$) 1595, 1467, 1248, 1012, 760
Elementary analysis:
Calculated C:49.56;H:2.38;N:8.26;S:18.90 Found C:49.60;H:2.34;N:8.25;S:18.88

EXAMPLE 2

67.2 g (0.250 mol) of 2,2'-dicyanodiphenyl disulfide and 150 g of chlorobenzene were placed in a 300 ml four-neck flask equipped with a stirrer, a thermometer, a dropping funnel and a condenser and 84.0 g (0.525 mol) of bromine was added dropwise at about 80° C. over one hour while stirring. The excess bromine was removed with an aqueous sodium carbonate solution, followed by crystallization with cyclohexane to obtain 101.9 g of white crystals, which were identified to be 2-cyanobenzenesulfenyl bromide from the following data. The yield starting from 2,2'-dicyanodiphenyl disulfide was 95.2%.

Physical properties
2-Cyanobenzenesulfenyl bromide
Appearances: white crystals
Melting point: 59.5°–60.5° C.
NMR: δ (ppm) 7.38–8.07 (m)
IR: (KBr, cm$^{-1}$) 1589, 1462, 1242, 958, 760
Elementary analysis:
Calculated C:39.27;H:1.88;N:6.54;S:14.98 Found C:39.32;H:1.88;N:6.52;S:15.00

EXAMPLE 3

74.5 g (0.500 mol) of 2-cyanophenyl methyl sulfide and 250 g of chlorobenzene were placed in a 500 ml four-neck flask equipped with a stirrer, a thermometer, a dropping funnel and a condenser and 96.0 g (0.600 mol) of bromine was added dropwise thereto at about 100° C. over five hours while stirring. The excess bromine was removed with an aqueous sodium carbonate solution, followed by distillation under reduced pressure to obtain 90.4 g of 2-cyanobenzenesulfenyl bromide. The yield starting from 2-cyanophenyl methyl sulfide was 84.5%.

EXAMPLE 4

86.2 g (1.00 mol) of piperazine and 7.5 g of chlorobenzene were placed in a 500 ml four-neck flask equipped with a stirrer, a thermometer, a dropping funnel and a condenser and 42.4 g (0.25 mol) of molten 2-cyanobenzenesulfenyl chloride was added dropwise thereto at about 130° C. over one hour while stirring, followed by stirring for four hours to complete the reaction. The excess piperazine was removed with water, followed by acidification with hydrochloric acid and extraction into the aqueous layer. The aqueous layer was basified with an aqueous sodium hydroxide solution to obtain 40.9 g (m.p.: 89°–90° C.) of 3-(1-piperazinyl)-1,2-benzisothiazole as crystals. The yield starting from 2-cyanobenzenesulfenyl chloride was 74.7%.

EXAMPLE 5

The same manner as that in Example 4 except for the use of 2-cyanobenzenesulfenyl bromide in stead of 2-cyanobenzenesulfenyl chloride as a raw material afforded, after cooling of an aqueous solution acidified with hydrochloric acid, 46.6 g of 3-(1-piperazinyl)-1,2-benzisothiazole hydrochloride as crystals (decomposition temperature 275°–280° C.). The yield starting from 2-cyanobenzenesulfenyl chloride was 73.0%.

EXAMPLE 6

74.5 g (0.500 mol) of 2-cyanophenyl methyl sulfide and 250 g of chlorobenzene were placed in a 500 ml four-neck flask equipped with a stirrer, a thermometer, a dropping funnel and a condenser and 96.0 g (0.600 mol) of bromine was added dropwise thereto at about 100° C. over five hours while stirring, followed by stirring for two hours to complete the reaction. The excess bromine was removed with an aqueous sodium carbonate solution and the solvent was distilled off to obtain 92.0 g of crude 2-cyanobenzenesulfenyl bromide. Separately, 172.4 g (2.00 mol) of piperazine and 15 g of chlorobenzene were placed in a 1000 ml four-neck flask equipped with a stirrer, a thermometer, a dropping funnel and a condenser and the molten crude 2-cyanobenzenesulfenyl bromide obtained above was added dropwise thereto at about 130° C. over one hour while stirring, followed by stirring for five hours to complete the reaction. The excess piperazine was removed with water and reaction mixture was acidified with hydrochloric acid, followed by extraction into an aqueous layer. The aqueous layer was basified with an aqueous sodium hydroxide solution to obtain 65.9 g of 3-(1-piperazinyl)-1,2-benzisothiazole as crystals. The yield starting from 2-cyanophenyl methyl sulfide was 60.2%.

EXAMPLE 7

The same manner as that in Example 5 except for the use of 100 g (1.00 mol) of N-methylpiperazine in stead of piperazine afforded 55.9 g of 3-(4-methyl-1-piperazinyl)-1,2-benzisothiazole hydrochloride as crystals, m.p.: 250°–252° C. The yield starting from 2-cyanobenzenesulfenyl bromide was 83.0%.

What is claimed is:

1. A process for preparation of 3-substituted benzisothiazole represented by the general formula (IV):

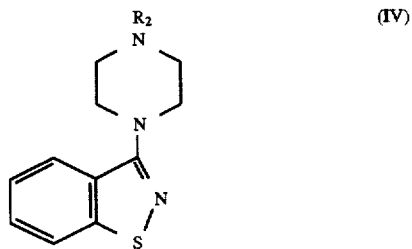

wherein $R_2$ represents H, alkyl group having 1 to 6 carbon atoms or substituted alkylene group having 1 to 6 carbon atoms, which comprises reacting 2-cyanobenzenesulfenyl halide represented by the general formula (I) with a piperazine compound represented by the general formula (III):

wherein $R_2$ is as defined for the general formula IV.

2. The process according to claim 1, wherein the piperazine compound represented by the general formula (III) is piperazine.

3. A process for preparation of 3-substituted benzisothiazole represented by the general formula (IV), which comprises halogenating a 2-cyanophenylthio derivative represented by the general formula (II) to obtain 2-cyanobenzenesulfenyl halide represented by the general formula (I), then reacting the halide represented by the general formula (I) with a piperazine compound represented by the general formula (III).

4. The process according to claim 3, wherein 3-substituted benzisothiazole represented by the general formula (IV) is 3-(1-piperazinyl)-1,2-benzisothiazole.

* * * * *